United States Patent [19]
Larson et al.

[11] Patent Number: 5,297,543
[45] Date of Patent: Mar. 29, 1994

[54] MEDICATION INHALER MIXER

[75] Inventors: Douglas A. Larson, River Forest; Thomas J. Danowski, Hoffman Estates, both of Ill.

[73] Assignee: Healthscan Products, Inc., Cedar Grove, N.J.

[21] Appl. No.: 903,611

[22] Filed: Jun. 24, 1992

[51] Int. Cl.⁵ .............................. A61M 11/00
[52] U.S. Cl. ..................... 128/200.23; 128/203.23; 128/203.12; 128/200.14
[58] Field of Search ............... 128/200.14, 200.23, 128/203.23, 203.24, 203.12, 204.25, 207.14

[56] References Cited

U.S. PATENT DOCUMENTS

| | | | |
|---|---|---|---|
| 2,788,784 | 4/1957 | Birch et al. | 128/200.23 |
| 4,150,071 | 4/1979 | Pecina | 261/78 A |
| 4,374,813 | 2/1983 | Chen et al. | 423/242 |
| 4,462,397 | 7/1984 | Suzuki | 128/200.14 |
| 4,484,577 | 11/1984 | Sackner et al. | 128/203.28 |
| 4,534,343 | 8/1985 | Nowacki et al. | 128/200.23 |
| 4,865,817 | 9/1989 | Burgess et al. | 422/168 |
| 4,926,852 | 5/1990 | Zoltan et al. | 128/200.23 |
| 4,938,210 | 7/1990 | Shene | 128/203.12 |
| 4,940,051 | 7/1990 | Lankinen | 128/200.18 |
| 4,953,547 | 9/1990 | Poole, Jr. | 128/203.12 |
| 5,040,527 | 8/1991 | Larson | 128/200.23 |
| 5,054,478 | 10/1991 | Grychowski et al. | 128/200.21 |
| 5,072,726 | 12/1991 | Mazloomdoost et al. | 128/200.14 |
| 5,078,131 | 1/1992 | Foley | 128/203.15 |
| 5,115,803 | 5/1992 | Sioutas | 128/200.23 |
| 5,178,138 | 1/1993 | Walstrom | 128/200.23 |

FOREIGN PATENT DOCUMENTS

| | | | |
|---|---|---|---|
| 251443 | 1/1988 | European Pat. Off. | 128/200.23 |
| 239338 | 5/1949 | United Kingdom | |

OTHER PUBLICATIONS

Ace Brochure of Demolding Healthcare Division of Jul. 17, 1991.

*Primary Examiner*—Edgar S. Burr
*Assistant Examiner*—Eric P. Raciti
*Attorney, Agent, or Firm*—Schweitzer Cornman & Gross

[57] ABSTRACT

A device for blending a medication with an airflow intended for inhalation, such as may be provided by a ventilator circuit is in the form of a tubular body intended to be placed in series with the ventilator line. The body is provided with a reduced-diameter portion which accelerates the airflow therethrough. Medication is ejected into the accelerated airflow in a direction contrary thereto, whereby increased dispersion and blending of the medication into the airflow results. The medication is then carried by the airflow to the patient.

6 Claims, 1 Drawing Sheet

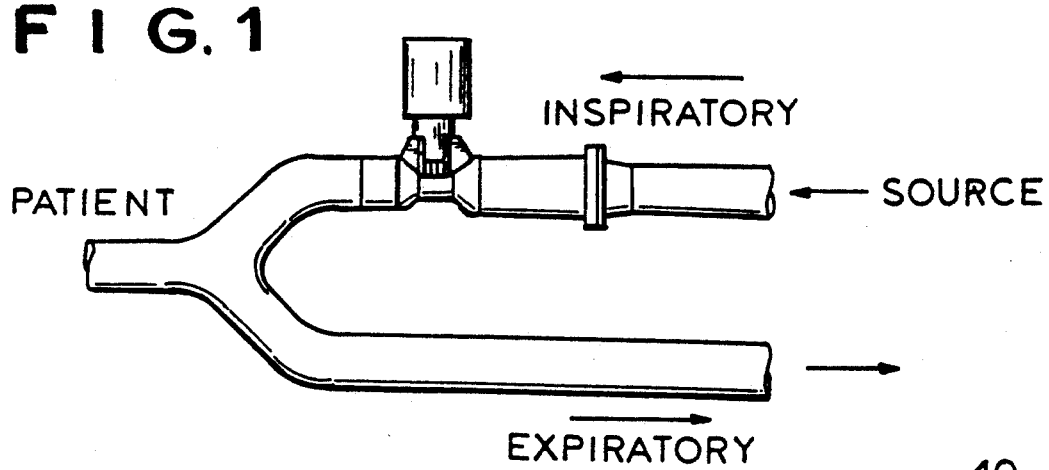
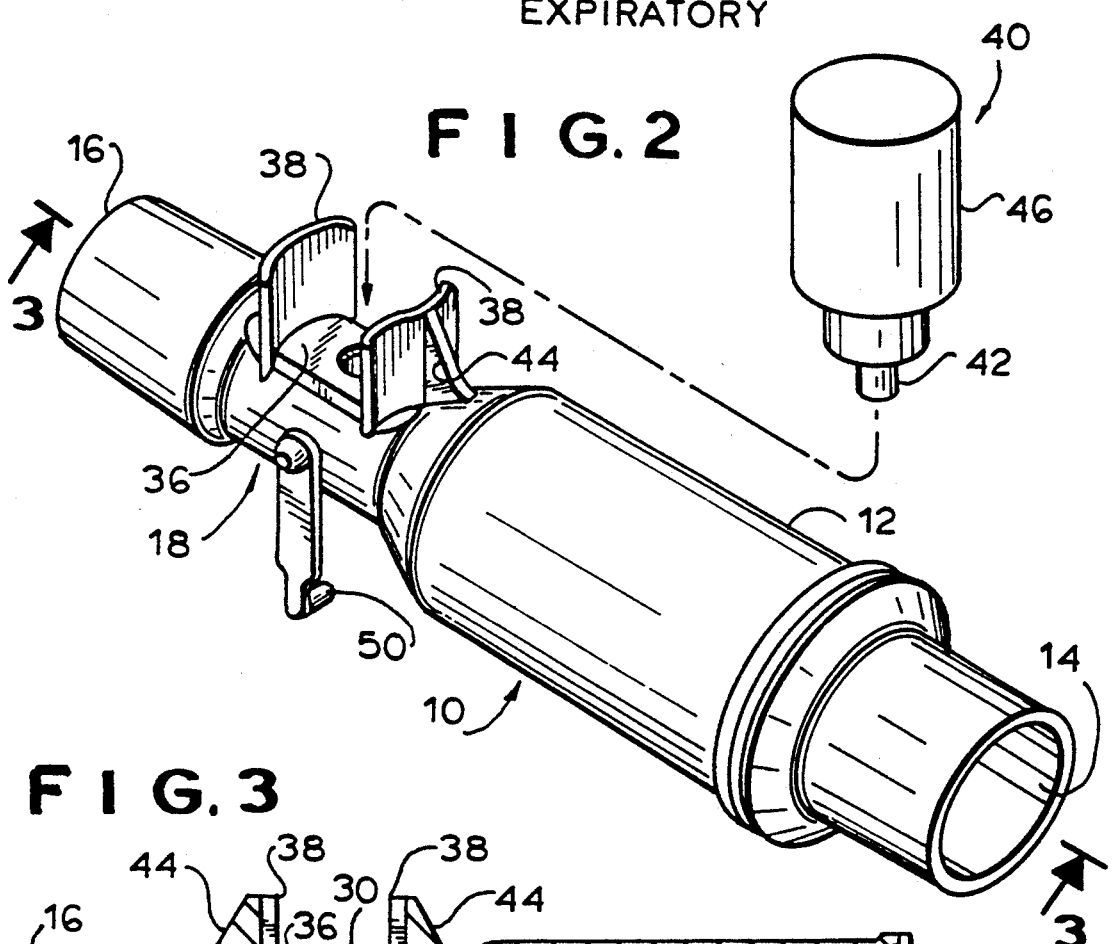
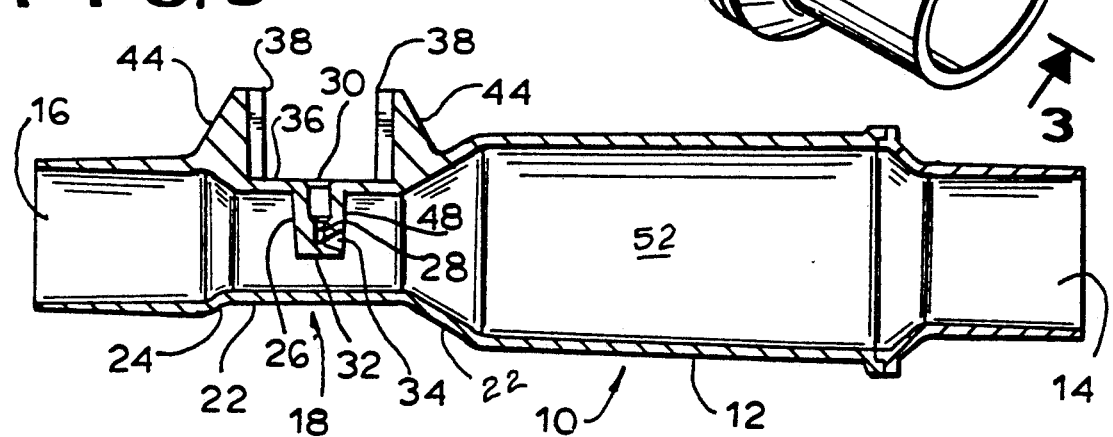

MEDICATION INHALER MIXER

The invention is directed to an apparatus for the mixing of a fluid, typically a vapor or finely dispersed mist, with a second fluid, typically a gas. In particular, the invention is directed to an apparatus for administration of a medication to a patient by introducing the medication into a gas flow intended to be inhaled by the patient.

BACKGROUND OF THE INVENTION

It is well recognized that, for certain medications, the most effective means of administration is in the form of a mist or plume inhaled by the user. In connection with the treatment of asthma, for example, such inhalation provides the most direct and effectual path to the lungs for bronchial dilation therapy, having substantial benefits over ingested or intravenous treatments. The inspiration of, for example, an epinephrine spray typically provides prompt and immediate relief.

There are a variety of mechanisms for use in conjunction with metered dose inhalation (MDI) dispensers, typically for asthma treatment, which are intended to permit the medication to be transported to the user's lungs during the inspiratory breath. In U.S. Pat. No. 5,040,527 of the present inventors and assigned to the assignee of record herein, a measured dose of medication from an MDI dispenser is directed against the flow of inspiratory air developed by the user. The medication release is timed to coincide with a rapid increase in such inspiratory flow. The resulting flow of inspiratory air contacting the oppositely-directed medication provides for mixing of the flows and the carrying of the medication deep into the lungs of the user.

The present invention is based upon the recognition by the inventors that the introduction of a counter-directed medication flow into a primary flow intended for inspiration can be used to improve the blending and dispensation of medication in a variety of situations, beyond that where the driving force for the inspiratory flow is developed solely by the breathing action of the patient.

BRIEF DESCRIPTION OF THE INVENTION

Accordingly, the present invention comprises an apparatus which may be installed in an otherwise conventional patient ventilator circuit or system to allow medication to be administered in conjunction with a supplied respiratory flow. The invention comprises a tubular body adapted for incorporation into a ventilator line, the body having a reduced-diameter portion in which the flow of the primary, ventilator-provided gas is locally increased in velocity Extending into the area of increased velocity is an open-ended medication administration tube, the open end of which is positioned to permit introduction of the medication into the main delivery tube in a direction opposed to the primary flow. The tube is adapted to be connected to a medication source. Upon introduction of a measured dose of medication into the primary flow, the two flows rapidly blend and combine, the primary flow carrying the medication to the patient, to be inhaled or otherwise made available for treatment or therapy purposes.

BRIEF DESCRIPTION OF THE DRAWINGS

A fuller understanding of the present invention and the features and operation thereof will be accomplished upon consideration of the following detailed description of a preferred, but nonetheless illustrative embodiment of the present invention when considered in conjunction with the annexed figures, wherein:

FIG. 1 is a diagrammatic representation of the present invention installed in a typical ventilator circuit;

FIG. 2 is a perspective view of the invention; and

FIG. 3 is a longitudinal cross-section taken along line 3—3 of FIG. 2;

DETAILED DESCRIPTION OF THE INVENTION

As depicted in the Figures, the present invention 10 is in the general form of a tubular body 12 having an inlet 14 and an exit 16 adapted to be compatible with conventional ventilator circuit tubing, such that the unit may be inserted into the ventilator line with leak-free connections. Towards this end, the inlet and outlet portions may be tapered and/or the unit may be provided with clamps or the like to seal and maintain the connections, and a one or multi-piece construction may be utilized. As presented in the Figures, matching female and male ends may be utilized at inlet 14 and outlet 16, respectively allowing the invention to be inserted into a respiratory line in a ventilator circuit having standard friction fit connectors, such as ANSI 22 mm couplings. Adaptors may be utilized in a conventional manner to couple the invention into other size lines.

A necked portion 18 is provided in the body, comprising a first inwardly-directed transition section 20, a reduced diameter straight interior section 22, and a rearward, outwardly-flaring transition section 24. It is to be recognized that a fluid flow through the body 12 from its inlet 14 to exit 16 develops a compressed flow through the necked portion 18, whereby the velocity of the fluid therethrough is locally increased. As shown in the Figures, the necked section may be located rearwardly of the longitudinal middle of the tubular body, whereby an elongated mixing chamber section 52 is defined in the area of the body forward of the necked portion.

Extending downwardly into the middle of interior section 22 is cylindrical stem 26, having a generally L-shaped hollow passageway 28 therein. The entrance 30 to the passageway opens the passageway to the exterior of the body and central section 22, while the leg 32 of the passageway and exit 34 are directed parallel to the main longitudinal axis of the tubular body 12 and are thus parallel to the general direction of flow therethrough. The exit 34 is through the portion of the surface of the stem facing the inlet 14, whereby fluid exiting the passageway 28 is directed in a direction opposed to that of the primary flow through the ventilator unit and the tubular body 12.

The passageway entrance 30 extends through an exterior pedestal surface 36, about which opposed shoulder walls 38 project upwardly. A pair of ribs 44 may be employed to support the shoulders. The opposed shoulder walls 38, in conjunction with pedestal surface 36, provide a seat and supporting mechanism for an MDI unit 40, shown displaced from the invention. The shoulders may thus be gently curved to more closely embrace the body portion of the MDI unit. The MDI unit 40 includes a nozzle stem 42, as known in the art, depression of which into the MDI bottle 46 providing for the release of a measured dose of medication outwardly through the nozzle.

To accommodate the nozzle and permit actuation of the MDI dispenser 40, the stem passageway 28 may be provided with an interior shoulder 48 against which the exposed end of the nozzle 42 rests, with the MDI body slightly elevated from the pedestal surface 36. Downward motion of the MDI bottle thus causes depression of the nozzle into the bottle and release of medication therethrough into the passageway 28. The shoulder is in the form of a 45 degree angle cone, allowing the tip of a standard metal-type MDI dispenser to seal against the shoulder during actuation.

Alternatively, the stem passageway 28 may be adapted to accommodate other medication dispensation means. This may comprise, for example, an elastomeric seal which can be punctured by a hypodermic needle, or a threaded or tapered fitting which can accept a tube through which appropriate medication is dispensed. To maintain efficiency of the ventilator circuit when a medication source is not affixed, a plug 50 may be utilized to seal the passageway entrance 30.

Operation of the ventilator circuit with the present invention in place is little different from operation without the medication-dispensation feature provided thereby. With the inlet and exit ports of the apparatus joined to the inspiratory side of the ventilator, the ventilator circuit is connected to a pressurized gas supply and to the patient in a conventional manner, and gas flow commenced. The primary gas flow is thus delivered to the patient in accordance with known methodology.

With a medication source coupled to the apparatus as previously disclosed, a measured dose thereof may be injected as required into the primary gas flow through the passageway 28. Because the velocity of the primary gas is increased in the area of the pedestal due to the constriction of flow, the medication ejected through passageway exit 28 is subject to a substantial opposed force from the primary flow. The contact between the counter-directed flows disperses the medication within the primary flow, avoids collection of the medication on the walls of the apparatus, and provides that the droplet size of the medication is decreased through increased evaporation of the MDI spray droplets, whereby the medication may be efficiently carried by the main flow to the patient for inhalation.

We claim:

1. Apparatus for combining a medication with a gas carrier for administration to a patient through a ventilator circuit, said ventilator circuit having a gas supply tube between a gas source and the patient, said apparatus comprising means for developing a continuing gas flow from said source through said supply tube; an elongated tubular body having opposed inlet and exit portions of diameters dimensioned and adapted to be inserted in series with said ventilator gas supply tube, means located between said inlet and exit portions adapted to accelerate said gas flow to an increased velocity between said inlet and exit portions and to return said gas flow to approximately its initial velocity upon exiting from said exit portion, a stem projecting inwardly from said tubular body upstream of said exit portion, said stem having a hollow passageway therein with an entrance exterior to said tubular body and an exit within said tubular body facing said inlet portion within the path of the accelerated gas flow; and means for introducing a pressurized flow of fluid medication into said tubular body through said stem passageway subsequent to the initiation of a flow of carrier gas through said tubular body and while the gas from said source is passing through said tubular body from said inlet end to said outlet end whereby said medication is actively combined with the simultaneous counter-directed accelerated flow of gas and carried therewith to the patient.

2. The apparatus of claim 1, wherein said passageway entrance extends through a pedestal located upon the exterior of said tubular body adapted to receive a nozzled MDI dispenser.

3. The apparatus of claim 2, wherein said hollow passageway is adapted to accept the nozzle of said MDI dispenser and support said MDI dispenser.

4. The apparatus of claim 1 further comprising means to selectively seal said hollow passageway.

5. A method of combining a medication with a primary gas flow provided through a ventilator circuit having a primary, pressurized gas supply connected through a ventilator tube to a patient, comprising the steps of:

accelerating the primary gas flow at a selected location in the ventilator circuit;

injecting the medication through a hollow stem into said accelerated flow in a direction opposite to the direction of said accelerated flow;

decelerating the mixture of the primary gas flow and the medication to approximately the initial velocity of the primary gas flow; and providing the combined primary gas and medication to the patient.

6. The method of claim 5, wherein said injection step comprises the activation of an MDI dispenser.

* * * * *